United States Patent [19]
Droege

[11] Patent Number: 5,248,198
[45] Date of Patent: Sep. 28, 1993

[54] METHOD AND APPARATUS FOR EVALUATING HEAT EXCHANGER EFFICIENCY

[76] Inventor: Thomas F. Droege, 2 S. 942 Thornecrest La., Batavia, Ill. 60510

[21] Appl. No.: 932,709

[22] Filed: Aug. 19, 1992

[51] Int. Cl.$^5$ ............... G01M 19/00; G01N 25/20
[52] U.S. Cl. .......................... 374/7; 73/112; 374/43
[58] Field of Search ............ 374/7, 43; 73/112; 165/36

[56] References Cited

U.S. PATENT DOCUMENTS

| | | |
|---|---|---|
| 2,330,599 | 9/1943 | Kuehni . |
| 3,095,739 | 7/1963 | Doolittle .................. 374/41 X |
| 3,913,378 | 10/1975 | Hausler ........................ 374/7 |
| 3,918,300 | 11/1975 | Weisstuch ................. 374/7 X |
| 4,024,751 | 5/1977 | Potrzebowski . |
| 4,527,908 | 7/1985 | Arisi ............................ 374/147 |
| 4,722,610 | 2/1988 | Levert et al. . |

FOREIGN PATENT DOCUMENTS

| | | |
|---|---|---|
| 0741126 | 6/1980 | U.S.S.R. . |
| 0855658 | 12/1960 | United Kingdom . |
| 1403950 | 8/1975 | United Kingdom . |
| 1423830 | 2/1976 | United Kingdom . |

Primary Examiner—Daniel M. Yasich
Attorney, Agent, or Firm—Allegretti & Witcoff, Ltd.

[57] ABSTRACT

This invention is a method for evaluating the type, extent, and threshold of fouling in a heat exchanger test tube by using a reference test block to measure a reference thermal relaxation time at a guaranteed clean reference section of a heat exchanger test tube and comparing the reference thermal relaxation time with thermal relaxation times measured at unclean sections of the heat exchanger test tube.

18 Claims, 2 Drawing Sheets

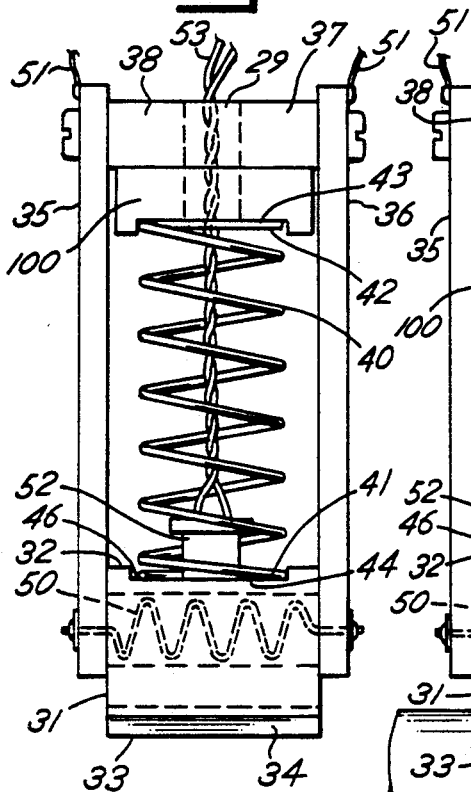
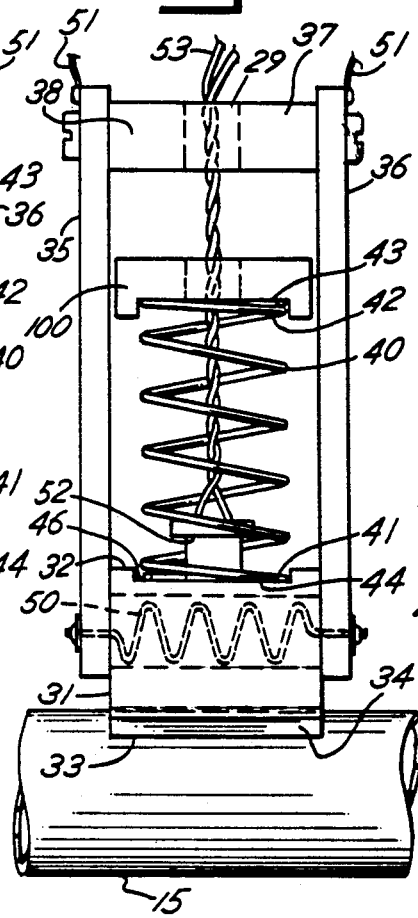
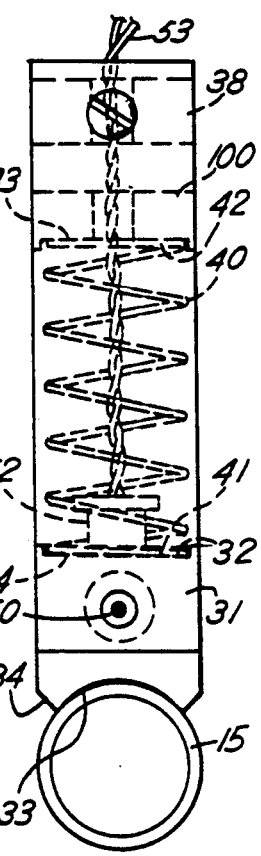
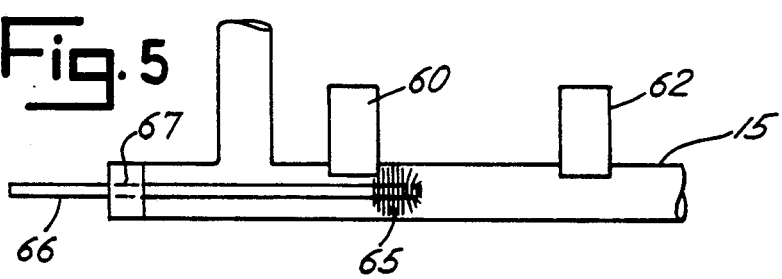
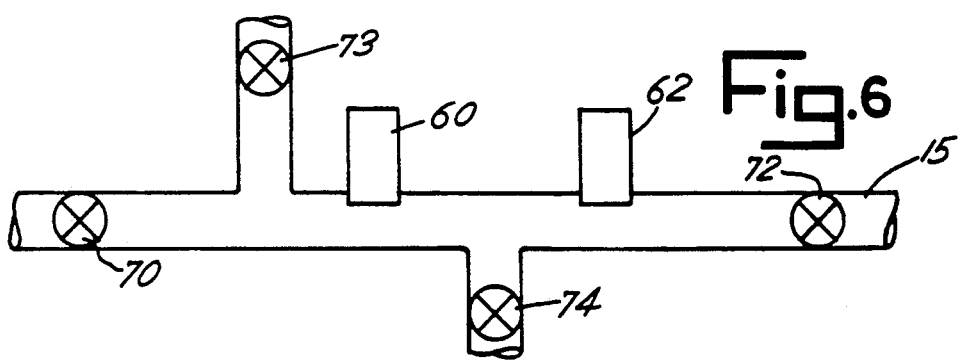

METHOD AND APPARATUS FOR EVALUATING HEAT EXCHANGER EFFICIENCY

BACKGROUND OF THE INVENTION

I. Field of the Invention

The present invention pertains to methods and an apparatus useful for determining the type, extent of, and thermal threshold of fouling in heat exchanger elements. The apparatus of this invention is capable of being easily installed and removed from the simulated side arm of various types of heat exchangers thereby facilitating the evaluation of the heat exchanger fouling.

In thermo dynamic apparatuses, such as heat exchangers, condensers, and the like, the formation of corrosion products, mineral, and organic deposits from various heating or cooling media can, over time, impair the thermal transmission or thermal resistance of the heat exchanger elements. The formation of corrosion products, mineral deposits, and organic deposits can be counteracted by intermittently cleaning the heat exchanger or through the controlled addition of fouling inhibiting additives to the heat exchange media. Cleaning the heat exchangers or chemical addition can be very expensive. To reduce these expenses, heat exchanger tubes are monitored to establish the presence of and the magnitude of fouling materials, and to evaluate the effectiveness of chemical addition. As a result of the monitoring, manual cleaning or chemical addition can be efficiently controlled.

The methods presently used to evaluate heat exchanger tube fouling rely greatly on balancing the flow rate of the heat exchange media through multiple heat exchanger test tubes. The methods produce inaccurate results when the flow rate of the heat exchanger media is unbalanced. Additionally, the monitorial methods presently used are generally incapable of identifying the type foulant.

II. Description of the Art

U.S. Pat. No. 2,330,599, to Kuehni, describes the basic principles for evaluating the thickness of a material using a thermal testing apparatus. The patent describes a thermal conductivity testing apparatus that includes a heat source and two resistance elements. One resistance element is placed into contact with a plate and the other is left uncontacted. The difference in the temperatures of the two resistance elements is monitored. The rate at which the temperature of the resistance monitor in contact with the plate decreases correlates to the thickness of the plate it touches.

Other patents also describe similar methods of measuring the thermal conductivity of fluids and other materials. These patents include United Kingdom Patents 1,423,830, 1,403,950 and 855,658. The '658 patent describes an apparatus for measuring the thermal conductivity of a test material using two probes mounted within an insulated block where one probe is contacted with the test material while the other probe remains isolated from the test material. The '830 patent describes an apparatus and method for measuring heat flux using a single probe. A single probe is exposed to a heat flux and the rate at which the probe increases in temperature is measured. The '950 patent describes a method for measuring the thermal diffusity of a sample by exposing a first surface of a sample to heat or radiation source while maintaining a second surface of a sample at a constant temperature. When the first surface is exposed to a heat or radiation pulse, the power necessary to maintain the second surface of a sample at the desired temperature is reduced. The power consumption is then correlated with the heat or radiation pulse magnitude to determine the thermal diffusivity of the sample.

U.S. Pat. No. 4,024,751 describes an apparatus for determining the heat transfer efficiency of a heat exchanger wall. The '751 patent recognizes that the efficiency of a heat exchanger is diminished by build up of materials and scale on heat exchanger wall surfaces. The claimed apparatus evaluates the magnitude of scale build up by heating the wall of a heat exchanger tube from first pre-determined temperature to a second pre-determined temperature, halting the heating, and measuring the time it takes for the temperature of the measured portion of the heat exchanger wall to drop from the second predetermined temperature to the first pre-determined temperature. The amount of time it takes to return from the second temperature to about the first temperature can be correlated to heat exchanger scale accumulation. The apparatus disclosed is a permanent apparatus including a heating means in direct contact with a heat exchanger tube.

U.S. Pat. No. 4,722,610 describes a monitor for determining the build up of slag on the flame side of water cooled walls of a coal-fired steam generator. The monitor includes a heater located adjacent to a thermocouple in a body. The thermocouple usually monitors the temperature of the body and when the body temperature decreases, this is an indication of slag build up. This indication is confirmed by heating the body with the heater, and measuring the temperature drop of the body using the same thermocouple. A slow drop in the temperature of the body indicates a large build up of slag.

Other apparatuses and methods for evaluating heat exchanger performance are known. However, the art lacks a method that uses a guaranteed clean reference as the basis for evaluating heat exchanger fouling.

SUMMARY OF THE INVENTION

A principle object of this invention is to provide a method for measuring heat exchanger performance that is useful in evaluating whether heat exchanger fouling is due to sedimentation, organic material build-up, or due to inorganic material build-up.

Another object of this invention is to provide a method for measuring heat exchanger performance that determines the extent of heat exchanger fouling.

Yet another object of this invention is to provide a method for measuring heat exchanger performance that determines the thermal threshold for fouling.

This invention relates generally to a method for evaluating fouling in a heat exchanger test tube containing a flowing fluid. According to one aspect of the method, a reference test block including a heater and a thermometer is contacted with a clean reference section of the heat exchanger test tube. The test block is heated to a temperature above that of the flowing fluid. The reference test block is allowed to cool providing a measurement of a reference thermal relaxation rate. Next, a measuring test block including a heater and thermometer is contacted with an unclean section of the heat exchanger test tube. The measuring test block is heated to a temperature above that of the flowing fluid and then allowed to cool. As the measuring test block cools, a measured thermal relaxation time is determined. The degree of fouling in the unclean section of the test tube is then determined by comparing the reference thermal relaxation time and the measured thermal relaxation time.

The method for evaluating heater exchanger fouling of this invention can be used to determine if heat exchanger fouling is caused by sedimentation by using three test blocks. A reference test block is contacted with a clean reference section of the heat exchanger test tube. A first measuring test block and second measuring test block are contacted with unclean sections of the heat exchanger test tube. The first measuring test block contacts a bottom dimension of the heat exchanger test tube while the second measuring test block is contacted with an opposite, top dimension of the heat exchanger test tube. Each test block is heated to a temperature above that of the flowing fluid and allowed to cool in order to determine a reference, a first, and a second thermal relaxation rate. Thermal relaxation rates indicating that the first test block is cooling at a slower rate than the second test block show that there is sedimentation fouling.

Another method of this invention is useful for determining the fouling thermal threshold. This method uses a reference test block and one or more measuring test blocks. The reference test block is used to measure the reference thermal relaxation time at a clean section of the test tube. A measuring test block is contacted with an unclean section of the test tube, i.e., a section of the test tube that has been operated at a heat load, and is maintained at a temperature above that of the flowing fluid. Occasionally, the heater heating the measuring test block is shut off and the actual relaxation time corresponding to the unclean section is measured. The thermal threshold of fouling, is found by measuring a series of thermal relaxation times when the measuring test block has been heated to various temperatures greater than the temperature of the flowing fluid. Thermal relaxation times indicating a decrease in fouling with increased temperature indicates the fouling due to organic deposits. Thermal relaxation times which indicate that fouling is increasing at increasing heater block temperatures indicates that a fouling is a result of nonorganic materials and these readings can be used to identify the temperature at which fouling will begin.

DESCRIPTION OF THE DRAWINGS

There is shown in the drawings a presently preferred embodiment of the invention wherein like numerals in the various figures pertain to like elements and wherein;

FIGS. 3 and 3A are front views of a test block assembly prior to and in contact with a test tube;

FIG. 4 is a side view of a test block assembly of this invention in contact with a test tube;

FIG. 5 depicts a mechanical device for producing a clean reference point in a test tube; and FIG. 6 depicts a chemical method for producing a clean reference point in a heat exchanger test tube.

DESCRIPTION OF THE CURRENT EMBODIMENTS

Figure 1:
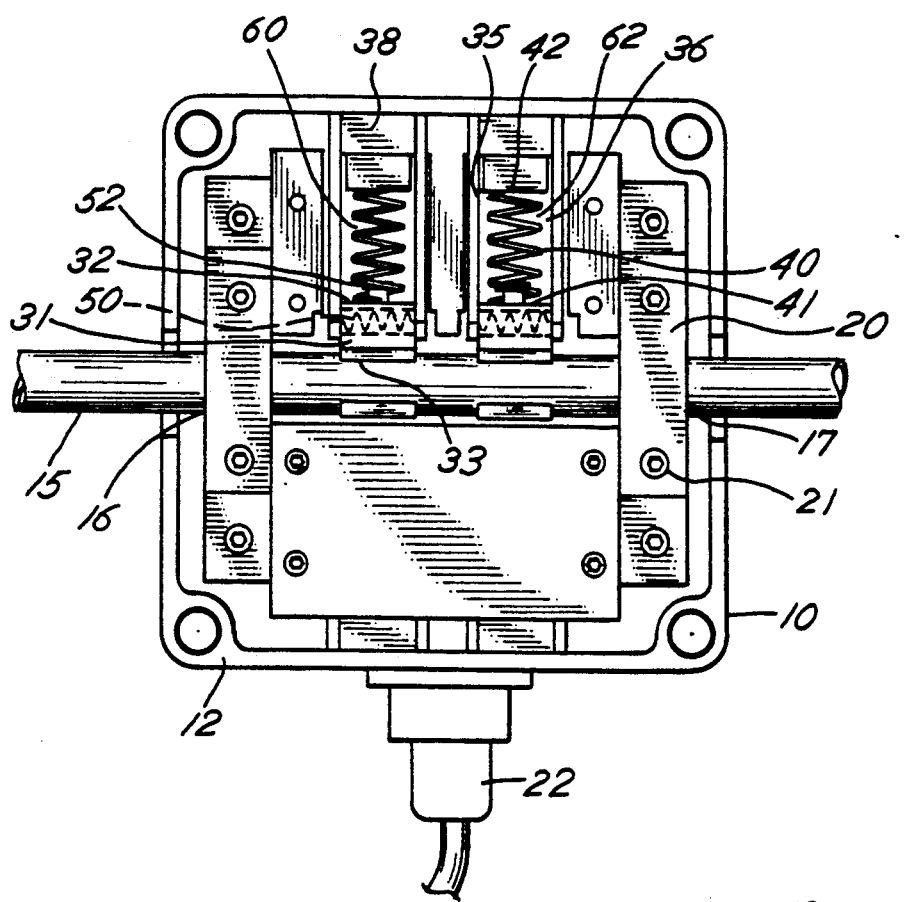
FIG. 1 is a front view of the portable monitor of this invention.

The present inventions relates to a method for determining the extent, type, and thermal threshold of fouling in heat exchanger tubes. The method utilizes a guaranteed clean reference measuring point. The guaranteed clean reference measuring point allows for the measurement of a reference thermal relaxation time in a heat exchanger test tube. The reference thermal relaxation time is then compared to thermal relaxation times measured at unclean points in the heat exchanger test tube in order to evaluate heat exchanger fouling.

A thermal relaxation time is essentially the time it takes for a heated block, in intimate contact with a heat exchanger test tube to drop from a first predetermined temperature, T1, above that of the fluid flowing in the heat exchanger test tube to a second predetermined temperature T2. Both T1 and T2 are greater than the temperature of the fluid in the heat exchanger test tube. The reference thermal relaxation time and the measured thermal relaxation time are compared. Typically, a change in ratio between the reference and measured thermal relaxation times can be correlated to fouling in the heat exchanger.

The thermal relaxation time is related to the ability of the heat exchanger tubes to transfer heat energy. As a the thermal relaxation time is being measured, the fluid in the heat exchanger test tube is removing the heat in a heated test block in intimate contact with the test tube causing the temperature of the test block to decrease. If the exchanger test tube is fouled, the fouling material provides resistance to this heat flow and the thermal relaxation time increases. Knowledge of the exact extent of the heat exchanger fouling is important when chemicals are being used to minimize heat exchanger fouling. By periodically determining thermal relaxation times, the ability of the chemical addition to inhibit or reduce existing heat exchanger fouling can be evaluated, and adjusted.

One problem encountered by measuring thermal relaxation times at an unclean section of a heat exchanger test tube is that the efficiency of the chemical addition, the minimum amount of chemicals needed to produce the desired result, cannot be measured. It is, of course, most desirable to inhibit heat exchanger fouling using the least amount of chemicals. Another problem suffered by current heat exchanger monitors is that they requirement that fluid flow rates be balanced through test tubes when a plurality of test tubes are used to measure the efficiency of chemical addition. The method of this invention eliminates the problems associated with unclean measuring points and the need to balance flow rates where multiple test tubes are used.

The method of this invention measures a reference thermal relaxation time at a section of the heat exchanger test tube that is guaranteed clean, i.e., where no fouling exists. At the guaranteed clean reference point, the thermal relaxation time is constant assuming all other process variables are constant. However, if flow rate, temperature, or flow composition of the flowing fluid change, then the reference thermal relaxation time will also change. One method to correct for changes in process variables is to electronically determine a flow rate in the heat exchanger test tube by using the reference thermal relaxation time. With the exact flow rate of the fluid in the heat exchanger test tube known, the measured thermal relaxation times can be corrected for flow rate differences to get a corrected thermal relaxation times which can be compared to previous measured thermal relaxation times to determine actual heat exchanger fouling. An alternate method is to periodically measure and update the reference thermal relaxation time.

The method of this invention can be used to determine the extent, type, and thermal threshold of heat exchanger fouling. The extent of heat exchanger fouling is determined using at least two test blocks, a reference test block and at least one measuring test block. The reference test block includes a thermometer and a heater. The reference test block is placed into intimate contact with the heat exchanger test tube such that the reference test block contacts as much of the surface of the heat exchanger test tube as is possible. The reference test block is placed into intimate contact with the heat exchanger test tube so that the reference test block contacts a controlled and unchanging section of the heat exchanger test tube. The mounting for the test block (shown in FIG. 1) allows the test block to freely move into square alignment with the test tube. The actual contact area is not critical, it is only critical that the contact area is fixed over the life of the measurement. This is accomplished by designing the test blocks so that they are free to "float" into alignment with the test tube, and not contact the test tube in cocked manner, that is, touching the test tube only at a point or a line. The effect of any imperfections in the surface of the test block or test tube is minimized by applying thermally conductive grease to the contact area.

The measuring test block is placed into intimate contact with an unclean portion of the heat exchanger test tube. When referring to a portion of the heat exchanger test tube as unclean, it is not meant that there is fouling in that section of the heat exchanger test tube. What is meant by the term "unclean," is that particular section of the heat exchanger test tube has not been cleaned in any way to guarantee that there is no fouling in that particular section.

A reference thermal relaxation time is measured by heating the reference test block, which is in intimate contact with the guaranteed clean section of the heat exchanger test tube to a temperature above that of the fluid flowing in the heat exchanger test tube. The reference test block is heated with the heater associated with the reference test block. The heating of the reference test block is discontinued and the temperature of the test block is allowed to drop. The thermal relaxation time then is the time it takes for the reference test block to cool from a predetermined temperature T1 to a predetermined temperature T2 with both T1 and T2 being above the test tube temperature. Ultimately, if allowed to cool completely, the reference test block will reach an equilibrium temperature about equivalent to the temperature of the flowing fluid in the test tube.

Next, the thermal relaxation time for an unclean portion of the heat exchanger test tube is measured. The measuring test block is heated with its integral heater to a temperature above that of the fluid flowing through the heat exchanger test tube. The heating of the measuring test block is discontinued and the measuring test block is allowed to cool. The thermal "measured" relaxation time of the measuring test block is then determined by determining the time it takes for the measuring test block to drop in temperature from a high predetermined temperature T1 to a low predetermined temperature T2. The reference and measured thermal relaxation times may be determined simultaneously or sequentially. It is preferred that the thermal relaxation times are determined simultaneously. The thermal relaxation times may be simultaneously determined as long as the test tube flow rate is high enough or the measuring points spaced far enough apart so that the measuring points are essentially thermally insulated from one another.

By occasionally allowing the test and reference blocks to cool all the way to the fluid temperature, a correction can be determined which is the error between the fluid reference test block thermometer and the measuring test block thermometer. This allows the reference test block thermometer to be used to determine the temperature reading that the measuring block would read if allowed to relax or cool all the way to the fluid temperature. This technique eliminates tracking errors between the test block thermometer and those in the test and reference blocks. The time constants can then be uniquely determined by T1, T2 and a fluid temperature measuring thermometer.

At this point the thermal relaxation time for the unclean portion of the heat exchanger test tube can be corrected for flow rate differences and other variables to define a corrected thermal relaxation time. The corrected thermal relaxation time can then be compared to other corrected thermal relaxation times or to the reference thermal relaxation time to determine whether fouling is present in the heat exchanger and the effect of the fouling on heat exchanger efficiency.

The method above is useful in determining the extent of fouling in the heat exchanger. Chemical addition to the heat exchanger can be modified in order to reduce or eliminate the fouling thereby increasing the efficiency of the heat exchanger. Subsequent measurements of reference thermal relaxation times and measured thermal relaxation times may be made to evaluate the effect of any changes in chemical addition.

A slightly different method is used to determine the type of fouling. There are at least two types of fouling that can be identified by methods of this invention. One type of fouling that can be identified is sedimentation fouling. With sedimentation, gravity causes particles in the flowing fluid to settle onto the bottom dimension, (in the direction of gravitational forces), of the heat exchanger test tube. This buildup of sediments on the bottom dimension of the heat exchanger test tube is in contrast to the top or opposite dimension of the test tube which is relatively free of foulants. Therefore, sedimentation can be identified by placing a first measuring test block into intimate contact with the top dimension of a heat exchanger testing tube and a second measuring test block into intimate contact with the bottom dimension of a heat exchanger testing tube. In this situation, where the thermal relaxation time of the top dimension is being compared to the thermal relaxation time of the bottom dimension, a reference thermal relaxation time is not a absolutely necessary. However, a reference relaxation time will always be necessary to correct the measured thermal relaxation times, so that they can be compared with measured thermal relaxation times taken at different fluid flow conditions.

To determine if sedimentation exists, a reference test block including a heater and a thermometer is contacted with the clean reference section of the heat exchanger test tube. The reference thermal relaxation time is then measured by heating the reference test block to a temperature above that of the flowing fluid, discontinuing the heating, and measuring the time it takes for the reference test block to decrease from a high predetermined temperature T1 to a lower predetermined temperature T2.

Next, a first measuring test block including a heater and thermometer is placed into intimate contact with the top dimension of an unclean section of the test tube while a second measuring test block including the heater and a thermometer is placed into intimate contact with the bottom dimension of the unclean section of the test tube. The first and second measuring test blocks are then heated sequentially, or in unison to a temperature above that of the fluid flowing in the heat exchanger test tube. The heating of the first and second measuring test blocks is then discontinued and time it takes for the first and second measuring test blocks to decrease in temperature from a first predetermined temperature T1 to a second predetermined temperature T2 is measured to obtain a first thermal relaxation time and a second thermal relaxation time. The first and second thermal relaxation times can then be compared, and if the second thermal relaxation time is much greater than the first thermal relaxation time then sedimentation fouling is indicated. The first thermal relaxation time and the second thermal relaxation times can also be corrected to obtain corrected first and second thermal relaxation times. The corrected thermal relaxation times can be compared with previous data to determine if there is any change in the fouling characteristics of the heat exchanger test tube.

The presence of organic foulants and the threshold foulant temperature can both be determined in a similar manner. However, the indications for each are not the same. The presence of organic foulants is indicated by a reduction in measured thermal relaxation times with increasing test block temperatures. On the other hand, the threshold temperature for fouling is determined by increasing the measuring test block temperature until the measured thermal relaxation times indicate an increase in fouling.

The method for evaluating the presence of organic foulants or determining the threshold fouling temperature begins by contacting a reference test block including a heater and a thermometer with a clean reference section of the heat exchanger test tube. A reference thermal relaxation time is then measured. Next, a measuring test block including a heater and a thermometer is placed into intimate contact with an unclean section of the test tube and the measuring test block is heated to a first test temperature above that of the flowing fluid. The first thermal relaxation time is then measured by discontinuing the heating of the measuring test block and measuring the time it takes for the measuring test block to decrease in temperature from a predetermined temperature T1 to predetermined temperature T2. Next, the measuring test block is heated to a second test temperature greater than the first test temperature and a second thermal relaxation rate is measured. The measuring test block is then heated to a third test temperature above that of the second and a third thermal relaxation time is measured. This process of increasing the test temperature and measuring thermal expansion times is repeated until the thermal relaxation rate increases, indicating the beginning of fouling, or decreases indicating that organic foulants are being destroyed by the hot test block and are being swept away from the walls of the heat exchanger test tube. In this method, it is the heated, moveable test block that actually causes or eliminates the fouling.

A second way to determine organic fouling is by the time development of the fouling. Scale formation tends to take long periods of time to develop significant change in heat transfer. Organic fouling on the other hand can be quite rapid. Therefore, dramatic changes in thermal relaxation over a short period of time are possible when the conditions become favorable for organic growth. Organic growth is also temperature sensitive, with optimum temperatures for different organic foulants being well known. With several blocks heated to temperatures known to be favorable for particular types of organic growth, it is possible to determine the type of organism and thus the optimum chemical treatment.

Another method for determining the presence of organic foulants or the threshold fouling temperature is to use a reference test block in conjunction with a plurality of measuring test blocks. The reference test block measures a reference thermal relaxation time while the plurality of measuring test block are kept in intimate contact with unclean portions of the heat exchanger test tube. The plurality of measuring test blocks are each continuously kept at temperatures above the temperature of the fluid flowing through the heat exchanger test tube. For example, if five measuring test blocks are contacted with the heat exchanger test tube then the first test block might be ten degrees above the fluid temperature, the second measuring test block twenty degrees above the fluid temperature, the third measuring test block kept at thirty degrees above the fluid temperature and so on. To evaluate the threshold fouling temperature or type of foulant, the thermal relaxation time for each of the plurality measuring test blocks is simultaneously or sequentially determined. A difference in the thermal relaxation time of one or more of the measuring test blocks will indicate the presence of organic foulants or the threshold fouling temperature. Based on these measurements, chemicals may be added or removed from the flowing fluid to eliminate organic fouling thereby promoting heat exchanger efficiency.

A second method of providing a heat load is to input constant power into the test blocks. Some devices, i.e., a steamcondenser, naturally output constant power per square foot of exchanger, this compares to putting constant power into a test block. Others, i.e. a water chiller, run at constant temperature differential and are best simulated by holding test blocks at constant temperature. Both methods have been used, and are simple to program into the typical computer based controller.

The test blocks do not cool exactly as an ideal, first order system does. In the simple first order case, the time constant is the time it takes for the temperature to drop to $1/e$ ($e=2.718$) of the difference between its initial and its final temperature. For example, suppose the test block is heated to 100 degrees above the water temperature. Time 1 would be the time when the test block is at 100 degrees and the heater has turned off. Time 2 would be when the test block reaches (100/e) or 36.78 degrees.

A first order system is completely determined if any two points and the final value are known. Thus the concern about correction of the final value by using the fluid temperature. By occasionally letting the test block cool all the way to the fluid temperature, the error in using the fluid temperature thermometer to define the ultimate cooled test block temperature can be determined. The advantage is that one thermometer can be used to "track" itself. By tracking it is meant that if both thermometers read the same at 20° C. they will also read the same at 30° C. and 40° C. This is unusual. Usually the thermometers will have slightly different scale factors so that if thermometer A and B read the same at 20° C., A might read higher than B at 30° C. and lower than B at 10° C.

If the block temperature and the fluid temperature are used to determine the heat transfer of the tube, then as the fluid temperature rises and drops the thermometer tracking error can produce a thermal conductivity error. With the present invention, the same thermometer measures the two temperatures and there is no first order since the thermometer tracks itself. There can be a second order error which is caused by using the fluid temperature thermometer to measure the final value the test block thermometer would reach if allowed to completely cool. This error is eliminated by intermittently allowing the test block thermometer to cool all the way to the water temperature and noting the $\Delta T$ between the cool test block temperature and the fluid temperature thermometer.

Unfortunately the test blocks do not behave exactly as first order systems. There is usually a range over which a test block will behave similarly to a first order system. The advantage of the first order system is that the same measurement is obtained regardless of the temperatures between which the two time measurements are taken so the measurement accuracy does not change as the time constant changes with fouling. The first order system is by definition the longest time constant. By waiting a while after the heater is turned off to mark the first temperature and time 0, the effects of higher order (faster) terms is minimized. It is preferred that the first time be measured after the temperature has dropped to 90% of the difference between the maximum heater block temperature and the test tube temperature and the second time be measures at 90 ($1/e$). The purpose of this measurement is to make the time constant measurement independent of the temperature or temperature difference. Thus T1 and T2 might be different for each of the blocks measured. But the ratios of T1 and T2 to the temperature difference of the particular block measured are the same for all the measured blocks. Normally $T1/T2=e$. But it might be 0.73e or 0.20e; any ratio would work.

The test tube may be cleaned by various means to produce a guaranteed clean heat exchanger test tube section. The cleaning may be done mechanically, chemically or ultrasonically. A mechanical means for cleaning a section of the test tube is shown in FIG. 5. FIG. 5 shows heat exchanger test tube 15 having an elbow. The reference test block 60 is located above a clean portion of test tube 10 while the measuring test block 62 is located above an unclean portion of test tube 10. The test tube 10 is cleaned using brush 65 which can be manually pulled back and forth in a section of the test tube using handle 66. Test tube 10 can be cleaned while fluid is flowing by virtue of seal 67 which prevents liquid from escaping test tube 10.

A chemical method for producing a guaranteed clean section of test tube 10 is shown in FIG. 6. Fluid typically flows through test tube 10 when first valve 70 and second valve 72 are opened. To clean the portion of test tube 10 associated with reference block 60, first valve 70 and second valve 72 are closed and third valve 73 and fourth valve 74 are opened. An acidic solution or some other cleaning solution is flushed through a portion of test tube 10 via third valve 73 and passes out of the test tube via fourth valve 74 to guarantee a clean test tube section for reference test block 60. The test tube section associated with measuring test block 62 is not cleaned.

A third method for producing a guaranteed clean reference section of the heat exchanger test tube is an ultrasonic cleaner associated with the reference test block. The ultrasonic cleaner can be intermittently or continuously operated to clean any foulants off the inner dimension test tube in the area where test block is in intimate contact with the test tube.

By no means are the methods for producing a guaranteed clean section of heat exchanger test tube mentioned above exclusive. Any other method in the art for cleaning only a section of a tube while leaving the remaining section of the tube unclean is within the scope of this invention.

The present method is preferably accomplished using a portable monitor that is capable of monitoring heat exchanger efficiency using a clean reference. The portable monitor of this invention is better understood by reference to FIGS. 1-4 which show various aspects of a preferred portable monitor and test block assembly of this invention.

Figure 2:
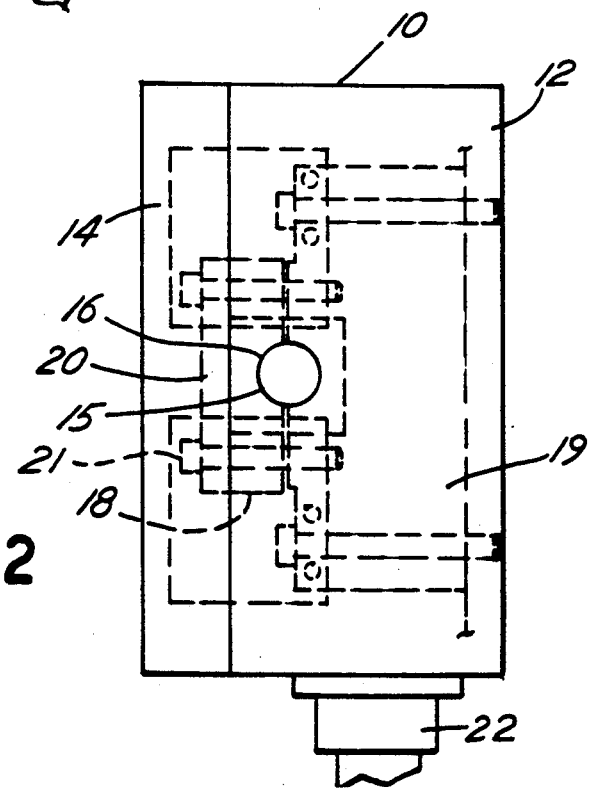
FIG. 2 is a side view of the portable monitor of this invention.

FIGS. 1 and 2 show front and side views respectively of the portable monitor of this invention. The portable monitor includes housing 10 comprising box 12 and box cover 14. FIG. 1, the front view of the portable monitor, shows the housing 10 with box cover 14 removed so that the contents of the housing are exposed. Housing 10 includes a first aperture 16 and a second aperture 17. The apertures may be located in the box 12 or in the box cover 14. A first aperture 16 and second aperture 17 located on opposite sides of the housing to define opposing apertures.

First aperture 16 and second aperture 17 provide a location where a test tube 15 can pass through housing 10 unimpeded. A test tube 15 is a standard feature on many heat exchangers. The test tube 15 mimics conditions occurring in the tubes contained in a multi-tube heat exchanger. The conditions that are mimicked include fluid temperature, fluid flow rate, fluid composition, and fluid pressure. Instead of being located in the heat exchanger, however, test tube 15 is located external to the heat exchanger. The portable monitor of this invention can be attached to test tube 15 in order to monitor the heat exchanger efficiency.

Housing 10 also includes supports 18 complementary to the first aperture 16 and the second aperture 17 for fixedly attaching the portable monitor of this invention to test tube 15. Supports 18 include a fixed support 19 which is attached to the housing and removable support 20 which is attached by fasteners 21 to fixed support 19. Fixed support 19 and removable support 20 include concave depressions on the dimension of the fixed support 19 and removable support 20.

An electrical connector 22 is integral to housing 10. Electrical connector 22 electrically links heaters, thermometers, and other electrical devices in housing 10 to source of electricity or to temperature or heater displays.

The purpose of housing 10 is to protect the test block assemblies 30 enclosed by the housing from the external environment. Housing 10 protects the test block assemblies 30 from tampering, from spills, and from other hazards that could potentially damage the test block assemblies or that could affect the accuracy of the data collected from the test block assemblies. The housing 10 can be purged with an inert gas if the test block assembly is located in an area that might be prone to explosions.

Referring now to FIGS. 3, 3A, and 4, one or more test block assemblies 30 are enclosed in housing 10. Each test block assembly 30 includes a movable test block 31 having a flat face 32 and a concave face 33. Movable test block 31 is located between parallel side supports which include a first side support 35 and a second support side 36. A stop block 38 is oriented perpendicularly to the parallel side supports and is fixedly attached to one extreme of first and second parallel side supports 35 and 36. A first end 41 of spring 40 is held in a depression 46 in flat face 32 of movable test block 31. A second end 42 of spring 40 is held in a depression in spring support 100. The spring 40 urges movable test block away from spring support 100.

First side support 35 and second side support 36 are perpendicularly attached to stop block 38 such that the first side support 35 and second side support 36 form parallel side supports. The first side support 35 and second side support 36 are fastened to spring support 38 and the test block 31 such that the entire assembly is free to move in all directions.

First side support 35 and second side support 36 are manufactured of a thin rigid material. The side supports act to guide the movement of movable test block 31. The side supports prevent movable test block 31 from moving laterally in relation to test tube 15. It is preferred that first side support 35 and second side support 36 are made of circuit board materials and are in fact themselves printed circuit boards. When the parallel side supports are circuit boards, they may include printed circuits for electrically uniting a heater 50, and thermometer 52 to heater leads and thermometer leads. The leads can then pass into electrical connector 22 which protects the leads outside of housing 10, and which unites the leads with a source of electricity and/or monitoring devices.

Movable test block 31 also has a concave face 33 opposite flat face 32. Concave face 33 contacts test tube 15 such that essentially the entire concave face 33 of movable test block 31 contacts a complementary convex surface of test tube 15. It is possible that test tube 15 will have a non-circular cross-section. In such a situation, the movable test block will not have a concave face but will have a face that is complementary to the geometry of test tube 15. However, it is preferred that test tube 15 have a circular cross-section and, as a result, the movable test block 32 will have a concave face.

The movable test block serves at least two purposes. The movable test block is made of a thermally conductive material that can be quickly heated to a desired controlled temperature. The movable test block also must remain in intimate contact with test tube 15 or to measure the ability of test tube 15 to remove heat from movable test block 31. Additionally, movable test block 31 can contain a thermometer 52. The conductive nature of movable test block 31 along with the fact that it is in intimate contact with test tube 15 ensures that the movable test block 31 will, except when heated, be at a temperature essentially identical to the temperature of the fluid in test tube 15.

Movable test block 31 can be made from any known conductive material. The best conductive materials are metals with a preferred conductive material being silver.

Movable test block 31 may include a heater 50, a thermometer 52, or both a heater and a thermometer. A preferred heater 50 is a resistance type heater which is generally located in a hole drilled through movable test block 31 parallel to test tube 15. Heater 50 is preferably attached by a heater lead to a printed circuit board which acts as one of the parallel side supports. Movable test block 31 can also include a thermometer 52. A preferred thermometer is a thermistor or a solid state semi-conductor transistor Model AD-590 manufactured by Analog Devices. Thermometer 52 is typically attached to flat face 32 of movable test block 31. A thermometer lead may unite thermometer 52 with a circuit board acting as a parallel side support. Alternately, the thermometer lead can pass through a hole in the spring support and run directly to electrical connector 22.

The portable monitor of this invention is attached to test tube 15 to monitor the efficiency of a heat exchanger associated with the test tube. In order to attach the portable monitor to a test tube, the box cover 14 must be removed from housing 10 to expose box 12 and one or more test block assemblies 30 located inside housing 10 in box 12. The fasteners 21 uniting removable support 20 with fixed support 19 are removed and removable support 19 is detached from support 18. Box 12 is oriented such that test tube 15 rests on the concave faces of the fixed support 19.

Stop block 38 prevents spring 40 from pushing test blocks 31 too far into the channel which receives test tube 15. A camber 34 on the edges of the test blocks 31 allows test tube 15 to be "snapped" into place. No finger pressure is required to urge test blocks 31 away from test tube 15. Camber 34 and the limited movement of the test block assemblies performs that function. During the "snap in" process, test block assemblies 30 are free to move in a very sloppy fit in the housing 10. This allows concave face 33 to become perfectly aligned with the test tube 15.

The portable monitor of this invention may include two or more test block assemblies 30 having movable test block 31 which includes a heater 50 and a thermometer 52. Preferably, one test block assembly will be the reference test block assembly including the reference test block. The remaining test block assembly or assemblies will be measuring test block assemblies. Measuring test block assembly includes a measuring test block for measuring the thermal relaxation time of an uncleaned section of a heat exchanger test tube. Alternatively, a plurality of portable monitors may be used to measure various thermal relaxation times.

The description above has been offered for illustrative purposes only, and it is not intended to limit the scope of the invention of this application which is defined in the following claims.

What I claim is:

1. A method for evaluating fouling in a heat exchanger test tube containing a flowing fluid comprising the steps of:
  a. contacting a first test block including a heater and a thermometer with an exterior dimension of the test tube corresponding to a portion of the test tube having a clean inner dimension;
  b. measuring a reference thermal relaxation time by heating the reference test block with the heater to a temperature above that of the flowing fluid, discontinuing the heating and measuring the time it takes for the reference test block to cool from predetermined temperature, T1, to predetermined temperature T2;
  c. contacting a plurality of measuring test blocks each including a heater and a thermometer with an exterior dimension of the test tube corresponding to a portion of the test tube having an unclean inner dimension;
  d. heating the plurality of measuring test blocks such that each of the plurality of measuring test blocks is at a different temperatures, and all measuring test blocks are at a temperature greater than the temperature of the flowing fluid;

e. maintaining the temperature of the plurality of measuring test blocks of step (d);

f. measuring a thermal relaxation time for each of the plurality of measuring test blocks by discontinuing the heating to each of the plurality of measuring test block and measuring the time it takes for each of the plurality of measuring test blocks to cool from predetermined temperature, T1, to predetermined temperature T2; and g. repeating steps (d)-(f).

2. The method of claim 1 wherein the threshold fouling temperature is determined by comparing each of the thermal relaxation times measured in step (f).

3. The method of claim 1 wherein there is a waiting period of from about 30 minutes to about 24 hours or more after heating step (d).

4. The method of claim 1 wherein the heat exchanger test tube is cleaned to define a clean reference section prior to contacting step (a).

5. The method of claim 4 wherein the heat exchanger test tube test is cleaned by directing a cleaning solution through a portion of the test tube.

6. The method of claim 4 wherein the heat exchanger test tube is cleaned with a mechanical cleaning means.

7. The method of claim 4 wherein the heat exchanger test tube is cleaned with an ultrasonic cleaner.

8. A method for evaluating fouling in a heat exchanger test tube containing a flowing fluid comprising the steps of:

a. cleaning a section of an inner dimension of the test tube to define a clean reference section;

b. contacting a reference test block including a heater and a thermometer with an exterior dimension of the test tube corresponding to clean reference section;

c. measuring a reference thermal relaxation time by heating the reference test block with the heater to a temperature greater than that of the fluid passing through the test tube, discontinuing the heating of the reference test block, and measuring the time it takes for the reference test block to cool from predetermined temperature, T1, to predetermined temperature T2;

d. contacting a first measuring test block including a heater and a thermometer with a top exterior dimension of the test tube corresponding to a portion of the test tube having an unclean inner dimension;

e. contacting a second measuring test block including a heater and a thermometer with a bottom exterior dimension of the uncleaned test tube corresponding to the portion of the test tube having an unclean inner dimension;

f. measuring a first thermal relaxation time corresponding to the top dimension of the unclean section of the test tube and a second thermal relaxation time corresponding to the bottom dimension of the unclean portion of the test tube; and g. determining the degree of fouling at the top dimension of the unclean portion of the test tube and at the bottom dimension of the unclean portion of the test tube.

9. The method of claim 8 wherein the top first thermal relaxation time and the second thermal relaxation time are compared to determine if the fouling is a result of silting.

10. The method of claim 8 wherein the reference thermal relaxation time is measured in step (c) by heating the reference test block with the heater to a temperature greater than that of the fluid passing through the test tube, discontinuing the heating of the reference test block, and measuring the time it takes for the reference test block to cool from predetermined temperature, T1, to predetermined temperature T2, where $T2 = T1(1/e)$.

11. The method of claim 8 wherein the first and second thermal relaxation times are measured in step (e) by heating the first and second measuring test blocks to a temperature greater than that of the fluid passing through the test tube, discontinuing the heating of the first and second measuring test blocks and measuring the time it takes for each the first and second measuring test blocks to cool from predetermined temperature, T1, to predetermined temperature T2, where $T2 - T1(1/e)$.

12. The method of claim 8 wherein the test tube is cleaned by activating an ultrasonic cleaning device associated with the first test block.

13. A method for evaluating fouling in a heat exchanger test tube containing a flowing fluid comprising the steps of:

a. contacting a reference test block including a heater and a thermometer with an exterior dimension of the test tube corresponding to a clean reference section of the test tube having a clean inner dimension;

b. measuring a reference thermal relaxation time by heating the reference test block with the heater to a temperature greater than that of the fluid passing through the test tube, discontinuing the heating of the reference test block, and measuring the time it takes for the reference test block to cool from predetermined temperature, T1, to predetermined temperature T2;

c. contacting a measuring test block including a heater and a thermometer with an exterior dimension of the test tube corresponding to a portion of the test tube having an unclean inner dimension;

d. measuring the thermal relaxation time of the unclean section of the test tube by heating the measuring test block with the heater to a temperature greater than that of the fluid passing through the test tube, discontinuing the heating of the reference test block, and measuring the time it takes for the reference test block to cool from predetermined temperature, T1, to predetermined temperature T2; and e. determining the degree of fouling in the unclean section of the test tube.

14. The method of claim 13 wherein the degree of fouling in the unclean section of the test tube is determined in step (c) by comparing the reference thermal relaxation time with the actual thermal relaxation time.

15. The method of claim 13 wherein the degree of fouling in the unclean section of the test tube is determined in step (e) by comparing a plurality of thermal relaxation times measured in step (d).

16. The method of claim 13 wherein a section of the test tube is cleaned prior to preforming step (a) to define a clean reference section.

17. The method of claim 16 wherein the test tube is mechanically cleaned.

18. The method of claim 16 wherein the test tube is cleaned by activating an ultrasonic cleaning device associated with the reference test block.

* * * * *